United States Patent [19]
Crane

[11] 4,264,152
[45] Apr. 28, 1981

[54] VISUAL STIMULUS DEFLECTOR

[75] Inventor: Hewitt D. Crane, Portola Valley, Calif.

[73] Assignee: SRI International, Menlo Park, Calif.

[21] Appl. No.: 14,989

[22] Filed: Feb. 26, 1979

[51] Int. Cl.³ ............................................... A61B 3/00
[52] U.S. Cl. ........................................ 351/1; 350/486
[58] Field of Search ...................... 351/30, 1; 350/285

[56] References Cited
U.S. PATENT DOCUMENTS 3,591,250  7/1971  Feinstein et al. ............... 350/285 X Primary Examiner—Paul A. Sacher
Attorney, Agent, or Firm—Urban H. Faubion

[57] ABSTRACT

A deflector, through which a subject views a target or visual stimulus, can independently move the visual stimulus horizontally and vertically to stimulate or compensate the subject's eye movement and can alter the optical distance to stimulate or compensate accommodation (focus). The target is projected on the subject's eye by way of two mirrors serially disposed in the projecting path and mounted for rotation about vertical and horizontal axes, respectively. Lens elements produce an undistorted unity magnification image of the eye at each mirror, with the center of rotation of the eye in each image nominally on the axis of rotation of the respective mirrors, and servo motors independently rotate the mirrors about their respective axes to produce vertical and/or horizontal deflection of the stimulus at the eye. The deflection mirror closest to the target is moved axially along the projected path, together with one of its imaging lens elements and the projected target or target image, to adjust spherical power and thereby stimulate or compensate accommodation.

6 Claims, 1 Drawing Figure

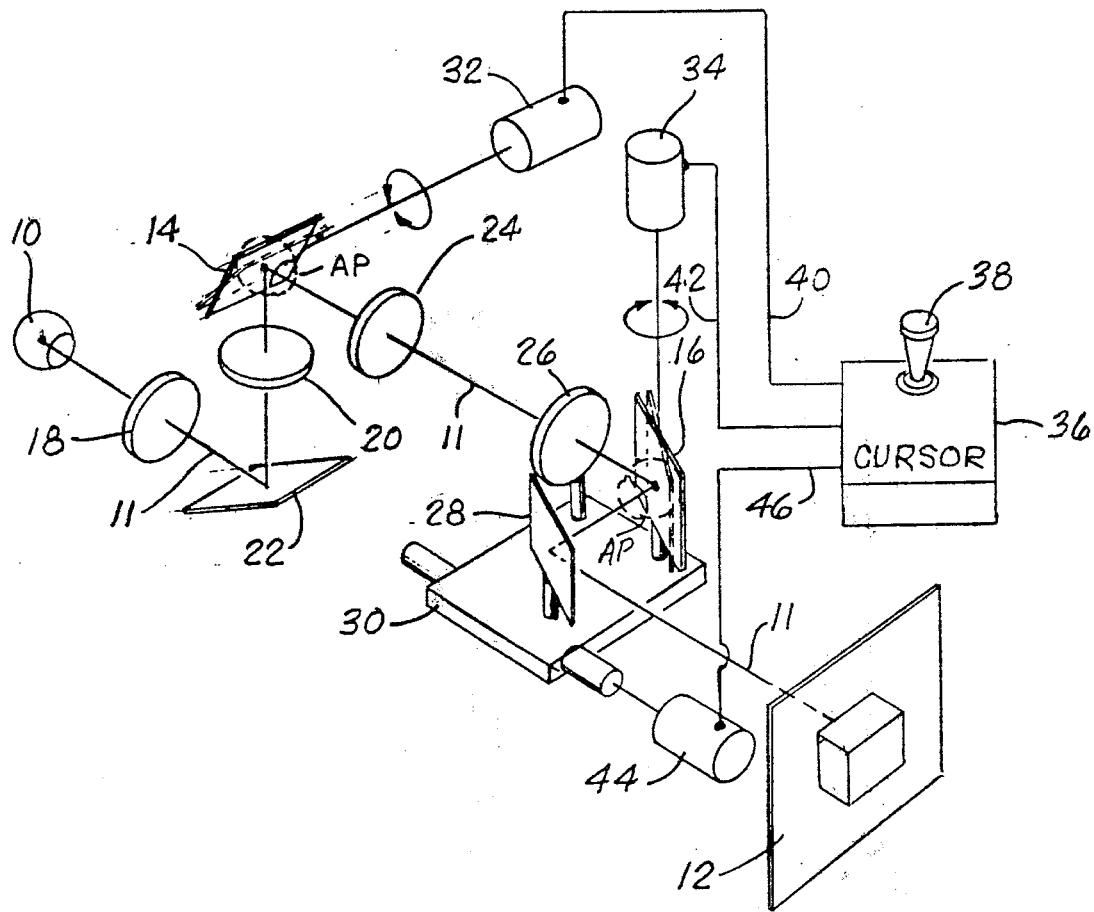
FIG_1

VISUAL STIMULUS DEFLECTOR

BACKGROUND OF THE INVENTION

The invention described herein was made in the course of work under a grant or award from the Department of Health, Education and Welfare.

This invention relates to a visual stimulator which presents a target to the eye and allows independent or concurrent movement of the target in three dimensions in order to stimulate or compensate eye movement and accommodation. That is, using the stimulator, the target can be given the appearance to the eye of moving horizontally, vertically or toward and away from the eye, either individually or simultaneously in any combination.

Detection of defects in the human visual system and defining proper correction of those defects often require movement of a target in specific ways to stimulate certain types of eye movements in the subject (patient). Response of a subject's eye to such target movements is also useful in developing an understanding of the response of the human visual system to stimuli and in diagnosing some physiological abnormalities.

Hewitt D. Crane, the present inventor, and Tom N. Cornsweet developed a visual focus stimulator which moves a target image toward and away from the subject's eye and thus stimulates focusing. Highly useful for observing powers of accommodation, this stimulator is described in "Ocular-Focus Stimulator" by Hewitt D. Crane and Tom N. Cornsweet, JOSA, v. 60, n. 4 (Apr. 1970), p. 577, "Visual Focus Stimulator Aids in Study of the Eye's Focusing Action", NASA Tech Brief 70-10568 (Nov. 1970), and also in connection with FIG. 5 of "Three-Dimensional Visual Stimulus Deflector" by H. D. Crane and Michael R. Clark, App. Optics, v. 17, n. 5 (Mar. 1, 1978), pp. 706–714 (see specifically pp. 708–709). This focusing stimulator, however, is only one dimensional. The present three dimensional stimulator is also described in the Applied Optics article, and the subject matter of the article is specifically incorporated herein by reference. The instrument provided by the present invention is the only visual stimulus deflector known to the inventor at the present time for stimulating eye movement in three dimensions.

SUMMARY OF THE INVENTION

It is an object of this invention to provide a visual deflector for testing the human visual system, which deflector can move the visual stimulus (target) horizontally and vertically as well as in apparent distance.

In visual testing, as in any scientific experiment, it is often important to be able to change one parameter at a time in order to be able to determine the effect of the individual parameters. Therefore, it is another object of the invention to provide such a deflector wherein the stimulus movements can be made individually and independently in each dimension.

Further, it is an object of this invention to provide such a deflector wherein the target image presented to the eye is undistorted by the deflection optics.

It is still another object of this invention to provide such a deflector wherein the brightness and visual angle subtended by the visual pattern or object remain fixed.

In carrying out the invention, a pair of spaced apart, rotatable mirrors is positioned serially in the path of a target image that is projected to the eye of a subject, and a nominally undistorted image of the eye, preferably a unity magnification image, is produced at each mirror, with the center of rotation of the eye images nominally located at the axes of rotation of the mirrors. The axes of rotation of the mirrors are oriented to sweep the image in directions perpendicular to each other at the eye in order to produce deflection in a plane perpendicular to the optical axes of the eye. The mirror closest to the target, along with at least part of the adjacent image forming means and at least an input image of the target, is moved axially along the path of the projected image between the two spaced apart, rotatable mirrors to produce image "deflection" along the optical axis of the eye (accommodation).

The novel features which are believed to be characteristic of the invention are set forth with particularity in the appended claims.

The invention itself, however, both as to its organization and method of operation, together with further objects and advantages thereof, may best be understood by reference to the following description taken in connection with the accompanying drawing.

BRIEF DESCRIPTION OF THE DRAWING

FIG. 1, the single FIGURE, is a perspective view and partially schematic diagram, illustrating the elements of a visual stimulus deflector according to a preferred embodiment of the invention.

DESCRIPTION OF PREFERRED EMBODIMENT

The overall three dimensional visual stimulus deflector illustrated is for the particularly stringent application where it is necessary to move a target in specific ways to stimulate certain types of eye movements in the subject (patient). The instrument described here can move the visual stimulus horizontally and vertically, as well as stimulate accommodation (focus) by altering the optical distance of the target from the subject, all without distorting the target image or affecting its brightness (intensity) or size. Horizontal and vertical movements and focus change are accomplished independently. Independent, three dimensional stimulation of both eyes is achieved by two such devices aligned side by side.

It is to be understood that this particular application is shown and described precisely because it has most exacting requirements. Many other applications of the principles involved are extant. For example, in some cases it is desirable to have an image or target (stimulus) follow the eye movements, and this deflector in cooperation with an eye tracker will provide such deflections. The use of basic elements and principles of the stimulus deflector is found in a beam stabilizer which forms part of a stabilized visual system and is disclosed and claimed in a copending patent application, Ser. No. 14,746, entitled STABILIZED VISUAL SYSTEM, filed Feb. 23, 1979 in the name of the present inventor and assigned to the assignee of the present application.

Referring specifically to the single figure, the subject's eye 10 is positioned in front of the visual deflector system to receive the target light 11, which is projected through the deflector from any two or three dimensional target, such as the illustrated target station or screen 12. The target image station 12, for the application illustrated here, remains fixed, and the apparent target movement is accomplished by the deflector system. Vertical and horizontal deflection of the image (as presented by the beam 11) at the eye 10 is based upon forming an essentially undistorted image (here a nominally unity magnification image) of the eye 10 with its center of rotation located nominally on the horizontal axis of rotation of a rotatably mounted vertical position deflection mirror 14 and another on the vertical axis of rotation of a rotatably mounted horizontal position deflection mirror 16. Note that the images of the eye 10 are shown in phantom at both the vertical and horizontal position deflection mirrors 14 and 16, respectively. Rotation of the vertical position deflection mirror 14 about its horizontal axis produces vertical movement of the visual field at the eye 10 without causing image distortion. Rotation of the horizontal position deflection mirror about its vertical axis produces horizontal movement of the visual field at the eye 10, again without image distortion.

The image of the eye 10 at vertical position deflection mirror 14 is formed by a pair of relay lenses 18 and 20, separated by the sum of their focal lengths and located nominally a focal length from the eye 10 and the axis of rotation of the vertical position deflection mirror 14, respectively. For the present application, the relay lenses 18 and 20 actually used are identical (50 mm), and this is preferred for practical reasons. A pair of identical lenses, separated by the sum of their focal lengths and similarly positioned, leads to a second optically conjugate, nominally undistorted unity magnification image. In order to redirect the beam 11 by 90° and give it a convenient direction relative to the eye 10, a stationary folding mirror 22 is provided between the relay lens pair 18 and 22 (at a 45° angle). The location of the folding mirror, although placed approximately a focal length from each of the relay lenses 18 and 22, is not critical and does not alter the optical characteristics of the system.

The undistorted unity magnification optically conjugate image of the eye 10 formed at the horizontal position deflection mirror 16 is provided by including a second pair of identical relay lenses 24 and 26, separated by the sum of their focal lengths and respectively located nominally a focal length from the axis of rotation of vertical position deflection mirror 14 and horizontal position deflection mirror 16. Thus, the unity magnification image of eye 10, which has its center of rotation nominally coincident with the axis of rotation of vertical position deflection mirror 14, is "relayed" to a corresponding position on the horizontal position deflection mirror 16, and the axes of rotation of both mirrors are nominally conjugate to the center of rotation of the eye 10.

The image from the target station 12 enters the deflection system by way of an input image deflecting mirror 28 which redirects the input image beam 11 by 90° and presents the image to the horizontal position deflection mirror 16, and consequently, to the eye 10 of the subject. Note here that the input image deflecting mirror 28, horizontal position deflection mirror 16 and the next closest lens 26 (nominally a focal length away) of the second relay lens pair (24 and 26) are all mounted on a focusing, or accommodation, platform 30 which is movable along the axis of the beam 11 from the target station. The reason for this arrangement is explained below in connection with accommodation, or optical focus. First, however, consider deflection of the visual field.

As previously pointed out, the axes of rotation of horizontal and vertical position deflecting mirrors 16 and 14, respectively, are nominally conjugate to the center of rotation of the eye 16. Thus, pure horizontal and vertical movement of the visual field (image 11) beam at the eye 16 is achieved without translation artifact, image distortion, or image size change by rotating the mirrors about their respective axes. In the embodiment illustrated, a pair of servo motors 32 and 34 is provided to rotate the respective vertical and horizontal position deflection mirrors about their axes, although adjustments may be made manually. As shown here, a cursor 36 having a joy stick 38 controls the vertical and horizontal driving servo motors 32 and 34, respectively. A pure up and down movement of the joy stick 38 (up and down as drawn) produces an output on vertical drive servo motor 32 via the cirucit to position the image field vertically. In similar fashion, the image field is positioned horizontally by horizontal deflection mirror 16 in response to a signal produced at its driving servo motor 34 via its circuit 42 when the joy stick 38 is moved sideways (in drawing). Since the unity magnification images of the eye 10 at vertical and horizontal position deflection mirrors 14 and 16 are optically conjugate, the pupil plane of the eye 10 has a conjugate plane (labeled AP for artificial pupil) at both of the position deflection mirrors 14 and 16. If a stop (not shown) smaller than the natural pupil is placed in the artificial pupil plane AP, it becomes the limiting aperture of the system; consequently, the effects of natural pupil changes are eliminated. Cylindrical and spherical correction lenses for each subject can be placed in a trial lens holder (also not shown) located in front of the aperture of the stop, and since plane AP is conjugate with the pupil plane of the eye, correction lenses placed near the artificial pupil plane AP have the same visual effect as if placed directly at the spectacle plane.

Simultaneous axial movement of the second lens 26 (of second relay lens pair 24 and 26), horizontal deflection mirror 16 and image deflecting mirror 28 adjusts the spherical power of the system without change in image position, size or brightness. This movement is accomplished by moving focus adjusting platform 30, to which all of these elements are affixed. Spherical power, in diopters, is linearly related to the axial position of the moveable carriage, which can be adjusted manually or, as illustrated, driven by a third (focus adjust) servo motor 44.

In the drawing the focus adjust servo motor 44, like the horizontal and vertical deflection servo motors 34 and 32, respectively, is driven from the ouptut of cursor 36. In this case, vertical pressure on the joy stick 38 of the cursor 36 produces a signal on its "focus adjust" output circuit 46. Thus, by proper movement of the joy stick 38, the image field can be moved independently or simultaneously in any one of three dimensions. It will also be appreciated that other arrangements can be made for driving the image field. For example, by a simple modification the stimulus pattern can be programmed by computer to provide any sequence of deflections.

In practice, it has been found desirable to use good quality (e.g., camera quality) lenses. It is believed that optical proofs and derivations are out of character here; they are found, however, in the Crane and Clark Applied Optics paper, op. cit.

It will be recognized that the objects of this invention have been carried out by considering the foregoing discussion along with the following characteristics of a system which has been built using the principles described. That is, a three dimensional visual stimulus deflector has been built which allows a subject to view any stimulus pattern or object through it, and the pattern (up to 25° in diameter) can be moved over a range of 40° horizontally and 30° vertically. The optical distance of the object being viewed can be changed over a 15 diopter range while the brightness and visual angle subtended by the object remain fixed. Further, the observer can view the object through a pupil of any desired shape and transmittance. Horizontal and vertical movements are independent, with time delays of 1 msec and a response range from dc to 200 Hz. Focus change is independent of lateral field motion and has a time delay of 12 msec and a maximum slewing rate of approximately 40 diopters/sec.

While particular embodiments of the invention have been shown and described here, it will, of course, be understood that the invention is not limited to these particular arrangements, since many modifications, both in the circuit arrangements and in the instrumentalities employed, may be made. For example, the order of the vertical and horizontal deflection mirrors 14 and 16 can be reversed, and other arrangements for driving the mirrors and focus adjust station may be readily made without departing from the scope of this invention. It is contemplated that the appended claims will cover any such modifications as fall within the true spirit and scope of this invention.

What is claimed is:

1. A visual stimulus deflector through which the image of a target is projected to the eye of a subject and which deflects the image field at the eye individually and simultaneously in three dimensions, including first and second spaced apart mirrors positioned serially in the path of the projected target image, each of said mirrors mounted for rotation about an axis therethrough, optical means for forming an image of the eye at each of the first and second mirrors, with the center of rotation of the eye in each image nominally at the axes of rotation of the said first and second mirrors, and first and second individual means to rotate the said first and second mirrors respectively about their axes, thereby to deflect the target image.

2. A visual stimulus deflector through which the image of a target is projected to the eye of a subject and which deflects the image field at the eye individually and simultaneously in three dimensions, as defined in claim 1 wherein the said optical means produces nominally undistorted and optically conjugate images at the axes of rotation of said first and second mirrors.

3. A visual stimulus deflector through which the image of a target is projected to the eye of a subject and which deflects the image field at the eye individually and simultaneously in three dimensions, as defined in claim 2, wherein the said optical means produces unity magnification images at axes of rotation of said first and second mirrors.

4. A visual stimulus deflector through which the image of a target is projected to the eye of a subject and which deflects the image field at the eye individually and simultaneously in three dimensions, as defined in claim 3, wherein the said optical means includes a first pair of relay lenses mounted in the path of the projected image between the eye and the said first mirror, the said first pair of lenses spaced by the sum of their focal lengths, the lens of the said first pair closest to the eye spaced nominally by its focal length therefrom and the lens of the said first pair closest to the said first mirror spaced nominally by a focal length from its axis of rotation; and a second pair of relay lenses mounted between the said first and second mirrors and spaced by the sum of their focal lengths from each other, the said second pair of lenses being positioned between the said mirrors so that the lens of the said second pair closest to each of the mirrors is spaced nominally by its focal length from the axis of rotation of the adjacent mirror.

5. A visual stimulus deflector through which the image of a target is projected to the eye of a subject and which deflects the image field at the eye individually and simultaneously in three dimensions, as defined in claim 4, wherein accommodation is provided by rigidly mounting together as a unit the said second mirror, the lens of said second lens pair which is adjacent the said second mirror and at least an image of the target, and providing means for moving the unit along a path parallel to the path of the projected image between said second and first mirrors.

6. A visual stimulus deflector through which the image of a target is projected to the eye of a subject and which deflects the image field at the eye individually and simultaneously in three dimensions, as defined in claim 4, wherein accommodation is provided by rigidly mounting a third mirror on a platform with said second mirror and the lens of said second lens pair in such a manner that the said third mirror reflects the target onto the said second mirror, and providing means for moving the said platform along the axial path of the projected image between said second and first mirrors.

* * * * *